(12) United States Patent
Gord et al.

(10) Patent No.: US 7,106,436 B1
(45) Date of Patent: Sep. 12, 2006

(54) TRIPLE-PUMP COHERENT ANTI-STOKES RAMAN SCATTERING SYSTEM

(75) Inventors: James R. Gord, Wright Patterson AFB, OH (US); Sukesh Roy, Dayton, OH (US); Robert P. Lucht, West Lafayette, IN (US); Michael S. Brown, Dayton, OH (US); Gregory J. Fiechtner, Livermore, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 422 days.

(21) Appl. No.: 10/726,360

(22) Filed: Dec. 3, 2003

Related U.S. Application Data

(60) Provisional application No. 60/430,880, filed on Dec. 4, 2002.

(51) Int. Cl.
   *G01J 3/44* (2006.01)
(52) U.S. Cl. ..................................... 356/301
(58) Field of Classification Search ................. 356/301
   See application file for complete search history.

(56) References Cited

U.S. PATENT DOCUMENTS 4,555,176 A * 11/1985 Moore et al. ............... 356/301
5,088,820 A * 2/1992 Winefordner et al. ...... 356/301
6,151,522 A * 11/2000 Alfano et al. ............... 356/301
2003/0007145 A1* 1/2003 Shimada ..................... 356/301

OTHER PUBLICATIONS

Hancock et al., "Dual-pump coherent anti-Stokes Raman scattering measurements of nitrogen and oxygen in a laminar jet diffusion of flame", Applied Optics, vol. 36, No. 15, pp. 3217-3226.*

* cited by examiner

*Primary Examiner*—Hwa (Andrew) Lee
*Assistant Examiner*—Kara Geisel
(74) *Attorney, Agent, or Firm*—AFMCLO/JAZ; Bobby D. Scearce

(57) ABSTRACT

A triple-pump coherent anti-Stokes Raman scattering (CARS) system for simultaneous measurements of temperature and species concentrations with high spatial and temporal resolution is described, wherein four laser beams generate CARS signals near two distinct wavelengths exhibiting an $N_2$ CARS signal along with the CARS signal from another target molecule, each pair of CARS signals generated over a relatively narrow wavelength region and captured with fixed-wavelength detection. Temperature and relative concentrations of the target species with respect to $N_2$ are extracted by fitting the measured CARS spectrum in each wavelength region.

5 Claims, 3 Drawing Sheets

TRIPLE-PUMP COHERENT ANTI-STOKES RAMAN SCATTERING SYSTEM

CROSS-REFERENCE TO RELATED APPLICATION

This application claims priority of the filing date of Provisional Application Ser. No. 60/430,880 filed 4 Dec. 2002, the entire contents of which are incorporated herein by reference.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to apparatus and methods for precision analysis of gaseous systems, and more particularly to a triple-pump coherent anti-Stokes Raman scattering (CARS) system for simultaneous measurements of temperature and species concentrations with high spatial and temporal resolution.

Complete characterization of reacting gaseous flow systems requires a determination of performance and chemical efficiency by measuring temperature and species concentrations either in the reaction zone or in the exhaust stream. Typically, these data are acquired utilizing several independent techniques executed serially, but the measurements would ideally be made simultaneously with a minimum number of diagnostic measurements.

Previously known CARS techniques have been used for temperature and multiple-species-concentration measurements, such as dual broadband rotational CARS (Martinsson et al, "Oxygen Concentration and Temperature Measurements in $N_2$—$O_2$ Mixtures using Rotational Coherent Anti-Stokes Raman Spectroscopy," *Applied Physics B* 62, 29–37 (1996); Thumann et al, "Simultaneous Temperature and Relative Nitrogen-Oxygen Concentration Measurements in Air with Pure Rotational Coherent Anti-Stokes Raman Scattering for Temperatures to as High as 2050 K," *Applied Optics* 36, 3500–3505 (1997); and Bood et al, "Temperature and Concentration Measurements in Acetylene-Nitrogen Mixtures in the Range 300–600 K using Dual-Broadband Rotational CARS," *Applied Physics B* 70, 607–620 (2000)) or simultaneous vibrational and rotational CARS (Yueh et al, "Simultaneous $N_2$, CO, and $H_2$ Multiplex CARS Measurements in Combustion Environments Using a Single Dye Laser," *Applied Optics* 27, 3233–3243 (1988); Bengtsson et al, "Combined Vibrational and Rotational CARS for Simultaneous Measurements of Temperature and Concentration of Fuel, Oxygen, and Nitrogen," *Applied Spectroscopy* 49, 188–192 (1995); Seeger et al, "Experimental Comparison of Single-Shot Vibrational and Dual-Broadband Rotational Pure Rotational Coherent Anti-Stokes Raman Scattering in Hot Air," *Applied Optics* 35, 2665–2671 (1996); and Brackmann et al, "Simultaneous Vibrational and Pure Rotational Coherent Anti-Stokes Raman Spectroscopy for Temperature and Multispecies Concentration Measurements Demonstrated in Sooting Flames," *Applied Optics* 41, 564–572 (1996)). However, the accuracy of the temperatures derived from rotational CARS measurements decreases with increasing temperature (Aldén et al, "Rotational CARS: a comparison of different techniques with emphasis on accuracy in temperature determination," *Applied Optics* 28, 3206–3219 (1989)).

The dual-pump CARS technique, first demonstrated by Lucht et al ("Measurements of Temperature and $CO_2$ Concentrations by Dual-Pump Coherent Anti-Stokes Raman Scattering," *AIAA Journal* 41, 679–686 (2003)) has been used for the simultaneous measurement of $N_2/O_2$ (see Lucht, "Three-Laser Coherent Anti-Stokes Raman Scattering Measurements of Two Species," *Optics Letters* 12, 78–80 (1987) and Hancock et al, "Dual-Pump Coherent Anti-Stokes Raman Scattering Measurements of Hydrogen and Oxygen in a Laminar Jet Diffusion Flame," *Applied Optics* 36, 3217–3226 (1997)), $N_2/H_2$ (Schauer, "Investigation of Flame Structure and Thermal Diffusion Effects in Hydrogen Jet Diffusion Flames," Ph.D. Thesis, Univ. of Illinois, Urbana Ill. (1998)), $N_2/CH_4$ (Green et al, "An Annular Phase-Matched Dual-Pump CARS System for the Simultaneous Detection of Nitrogen and Methane," *Applied Optics* 37, 1690–1701 (1998)), and $N_2/CO_2$ (Brüggemann et al, "CARS Spectroscopy for Temperature and Concentration Measurements in a Spark Ignition Engine," in *Combustion Flow Diagnostics*, by Duräom et al, eds., Kluwer Academic, Dordrecht, The Netherlands, 495–511 (1992)).

In a dual-pump CARS system, the wavelengths of the input beams are adjusted such that the CARS spectra for the two species under study are observed at nearly the same frequency. This arrangement largely eliminates the potential errors arising from wavelength-dependent variations in signal transmission or detector efficiency that can complicate other multiple-species CARS techniques such as dual-Stokes and dual-broadband CARS (Eckbreth, *Laser Diagnostics for Combustion Temperature and Species*, Gordon and Breach Publishers, Amsterdam, The Netherlands, (1988)).

The invention described and claimed herein solves or substantially reduces in critical importance problems with prior art techniques by providing a triple-pump CARS system for accurate measurement of temperature along with concentration of three species in high-temperature reacting flows. The invention permits monitoring of the local temperature and concentrations of two target species with respect to a reference species using a single hardware platform with high spatial and temporal resolution.

A triple-pump CARS system representative of the invention uses four laser beams to generate CARS signals near two distinct wavelengths. Both wavelength regions exhibit an $N_2$ CARS signal along with the CARS signal from another target molecule. Each pair of CARS signals is generated over a relatively narrow wavelength region and can be captured with fixed-wavelength detection. Temperature and relative concentrations of the target species (with respect to $N_2$) are extracted by fitting the measured CARS spectrum in each wavelength region. Because the $N_2$ concentration is typically initially known, the amplitude of the target-species signal relative to that of the paired $N_2$ signal provides an absolute measure of the target-species concentration. In demonstration of the invention, tests were performed in an atmospheric-pressure hydrogen-air diffusion flame, and the CARS signals from $N_2/O_2$ and $N_2/H_2$ pairings were acquired using two spectrometers each equipped with a charged coupled device (CCD) camera. For measurements made in reacting flows using air as the oxidizer, nitrogen is the most convenient reference molecule. Nitrogen CARS spectra are known over a very wide range of temperature and pressure.

It is a principal object of the invention to provide a system for analysis of gaseous systems.

It is a further object of the invention to provide an improved system and method for precision analysis of flowing gaseous systems.

It is another principal object of the invention to provide a triple-pump CARS system for simultaneous measurements of temperature and species concentrations with high spatial and temporal resolution.

These and other objects of the invention will become apparent as a detailed description of representative embodiments proceeds.

SUMMARY OF THE INVENTION

In accordance with the foregoing principles and objects of the invention, a triple-pump coherent anti-Stokes Raman scattering (CARS) system for simultaneous measurements of temperature and species concentrations with high spatial and temporal resolution is described, wherein four laser beams generate CARS signals near two distinct wavelengths exhibiting an $N_2$ CARS signal along with the CARS signal from another target molecule, each pair of CARS signals generated over a relatively narrow wavelength region and captured with fixed-wavelength detection. Temperature and relative concentrations of the target species with respect to $N_2$ are extracted by fitting the measured CARS spectrum in each wavelength region.

DESCRIPTION OF THE DRAWINGS

The invention will be more clearly understood from the following detailed description of representative embodiments thereof read in conjunction with the accompanying drawings wherein.

DETAILED DESCRIPTION

A discussion of technology related to the underlying principles of the invention may be found in technical papers contained in the related application referenced above, and entitled, "Triple-Pump Coherent Anti-Stokes Raman Scattering (CARS): Temperature and Multiple-Species Concentration Measurements In Reacting Flows," by Roy et al, *Optics Communications* 224, 131–137 (2003), and "Triple-Pump Coherent Anti-Stokes Raman Scattering for Simultaneous Temperature and Concentration Measurements," by Velur et al, the entire contents and teachings of which are incorporated by reference herein.

Figure 1:
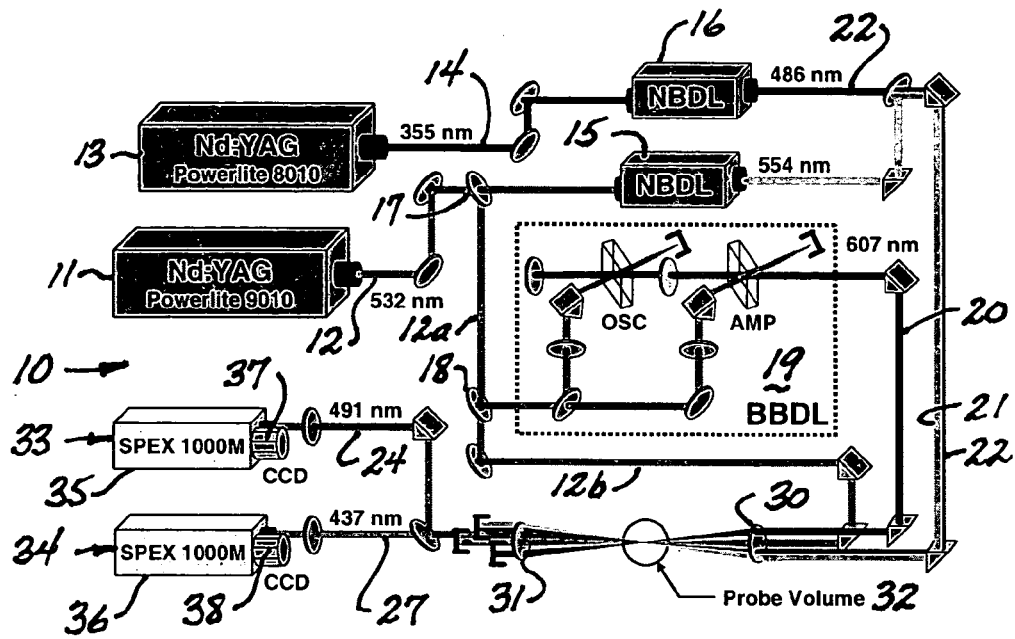
FIG. 1 is a schematic diagram of the essential components of the triple-pump CARS system according to the invention.
Figure 2:
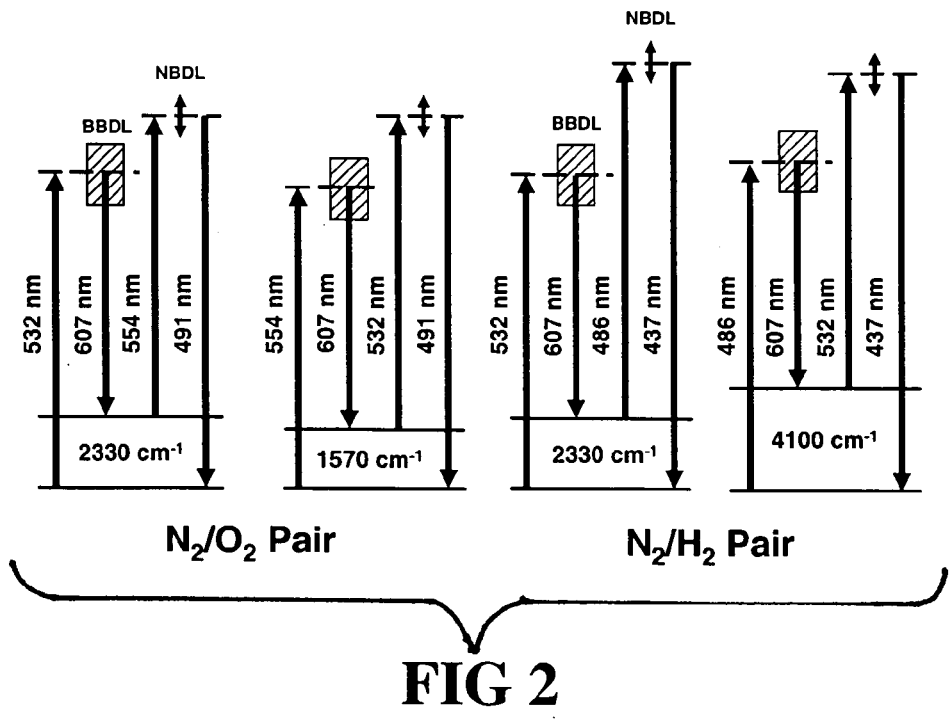
FIG. 2 shows an energy level diagram of the triple-pump CARS system.
Figure 3:
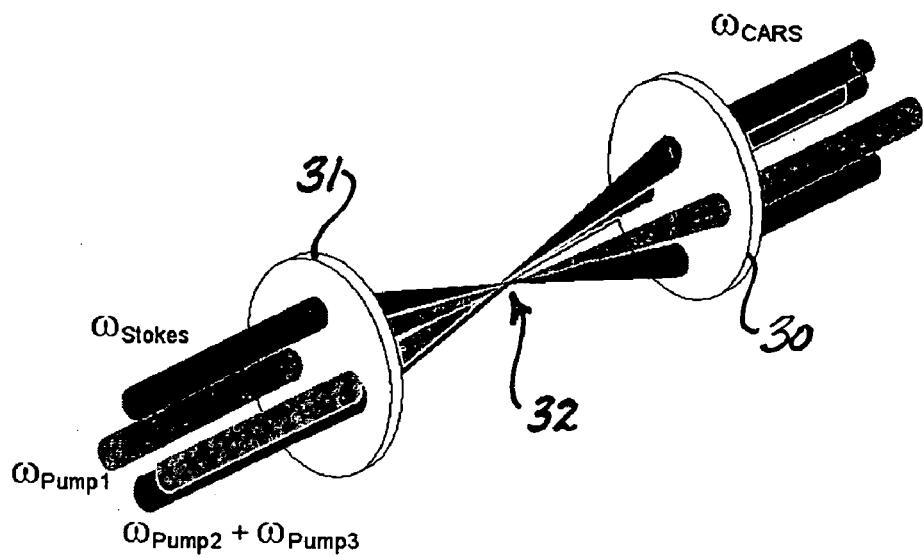
FIG. 3 is a phase-matching diagram of triple-pump CARS demonstrations of the invention.

Referring now to the drawings, FIG. 1 shows a diagram of the essential components of a representative embodiment 10 of the triple-pump CARS system according to the invention. In the representative system 10, an injection-seeded Nd:YAG laser 11 provides an output beam 12 at 532 nm of about 500 mJ/pulse and laser 13 provides an output beam 14 at 355 nm about 250 mJ/pulse, at 10 Hz (Continuum Powerlite Precision 8010). Lasers 11 and 13 pump respective narrowband dye lasers 15,16 at 532 nm and 355 nm, respectively. Additionally, laser 11, through suitable optics including beamsplitters 17,18 simultaneously pumps broadband dye laser (BBDL) 19 with beam 12a at 532 nm and provides a 532-nm CARS pump beam 12b. In the embodiment shown, the broadband dye laser 19 generates a Stokes beam 20 for each of four CARS signals with a frequency spectrum centered near 607 nm. Lasers 15,16 provide pump beams 21,22 at 554 nm and 486 nm for the $O_2$ and $H_2$ molecules, respectively. Referring now additionally to FIG. 2, shown therein is an energy level diagram of the triple-pump CARS system for the $N_2/O_2$ and $N_2/H_2$ pairs. The combination of the 532-nm pump beam 12a with the 607-nm Stokes beam 20 produces an $N_2$ Raman polarization that coherently scatters the 554-nm pump 15, yielding an $N_2$ CARS signal 24 near 491 nm. Simultaneously, pairing of the 554-nm pump 15 with the 607-nm Stokes beam produces an $O_2$ Raman polarization that scatters the 532-nm pump, yielding an $O_2$ CARS signal also appearing near 491 nm. The second narrowband dye laser 16 is pumped with the 355-nm laser beam 14 and generates a light beam 22 at 486 nm. An $N_2$ CARS signal 27 appearing near 437 nm is produced as the 486-nm beam 22 is scattered by the $N_2$ Raman polarization. An $H_2$ polarization arising from the combination of the 486-nm and 607-nm beams scatters the 532-nm beam, producing an $H_2$ signal also near 437 nm. The incident beams are phase-matched using the folded boxcars geometry with the 554-nm and 486-nm beams 21,22 arranged co-linearly. The phase-matching diagram for the triple-pump CARS system is shown in FIG. 3. The laser beams were focused and re-collimated using 300-mm focal-length lenses 30,31 defining probe volume 32 therebetween. With incident beam energies of about 15 mJ/pulse, CARS signals on the lean and rich sides of a hydrogen-air diffusion flame are easily detected with dwell times ranging from 0.5 sec to 20 sec.

Measurements in demonstration of the invention were performed using an atmospheric-pressure laminar hydrogen-air diffusion flame. System 10 used in the demonstration measurements included two spectrometer/CCD detector systems 33,34 for the detection of wavelengths 24, 27, 491 and 437 nm, respectively. The CARS signals 24,27 were dispersed by 1.0-m spectrometers (SPEX 1000M) 35,36 each equipped with a 2400 grooves/mm grating and charge coupled device (CCD) cameras 37,38. PixelVision UV-enhanced, back-illuminated, unintensified CCD cameras, each with an 1150×350-pixel array, were used for acquisition of the CARS spectra. The gain setting for the CCD was 4 electrons/count, and the quantum efficiency was approximately 70 to 80% for the 400–500 nm wavelength range. The limiting resolution of the spectrometers 33,34 was 0.16 $cm^{-1}$ at 491 nm and 0.21 $cm^{-1}$ at 437 nm. The spectral dispersion of the CCD detector systems 33,34 was 0.25 $cm^{-1}$/pixel.

The CARS spectra were normalized using a nonresonant spectrum to account for effects of pulse-to-pulse laser power fluctuations, long-term power drifts, and spectral variations in dye power (see Eckberth, supra). The nonresonant spectrum was recorded by flowing argon through a flow tube into the beam overlap (probe) region 32. The broadband-dye-laser spectrum was stable over the course of the experiment.

Figure 4:
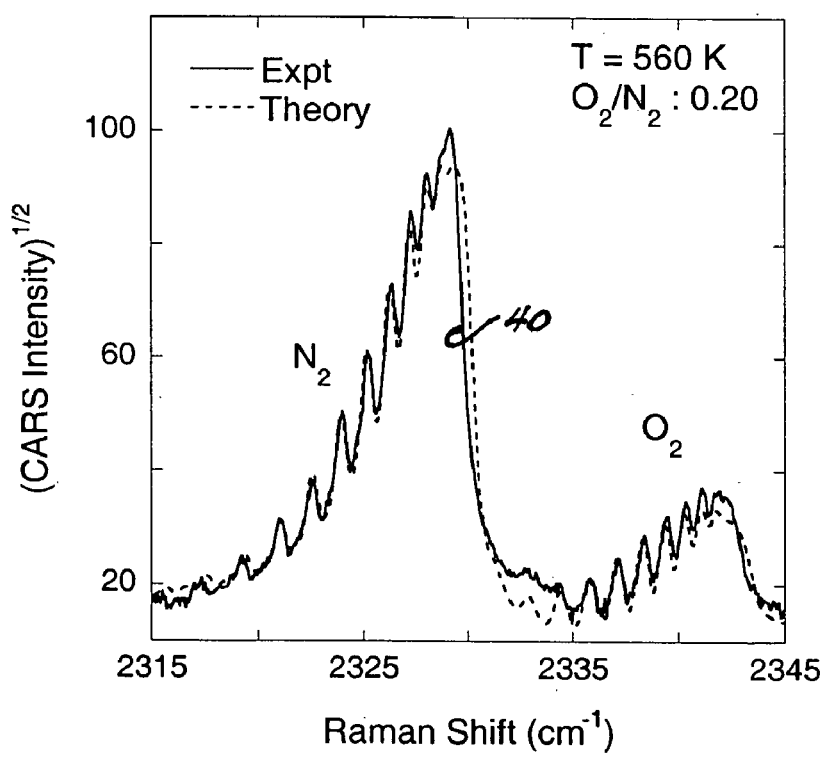
FIG. 4 is a $N_2$—$O_2$ CARS spectrum in an atmospheric-pressure hydrogen-air diffusion flame.

FIG. 4 shows an $N_2$—$O_2$ CARS spectrum (average of 100 laser shots) generated in an atmospheric-pressure hydrogen-air diffusion flame. Signals were generated through the combination of the 532-nm, 554-nm, and 607-nm incident beams. This signal appears near 491 nm, acquired on the lean side of the flame about 2 mm from the center of the nozzle and 0.5 mm above the nozzle lip, and the Raman shift is calculated based on the 554-nm laser beam. A dichroic was used to reject the stray laser light at 486 nm from the 491-nm CARS signal. A small amount of residual 486-nm light is present in the spectrum, but this scattered light can be substantially reduced in intensity using spectral filtering. For the spectrum shown in FIG. 4, the temperature and the relative concentration were evaluated by fitting the experimental CARS spectrum with a theoretical spectrum generated previously (see Palmer, *The CARSFT Computer Code for Calculating Coherent Anti-Stokes Raman Spectra: User and Programmer Information*, Sandia Nat'l Lab Report SAND89–8206 (1989)).

Figure 5:
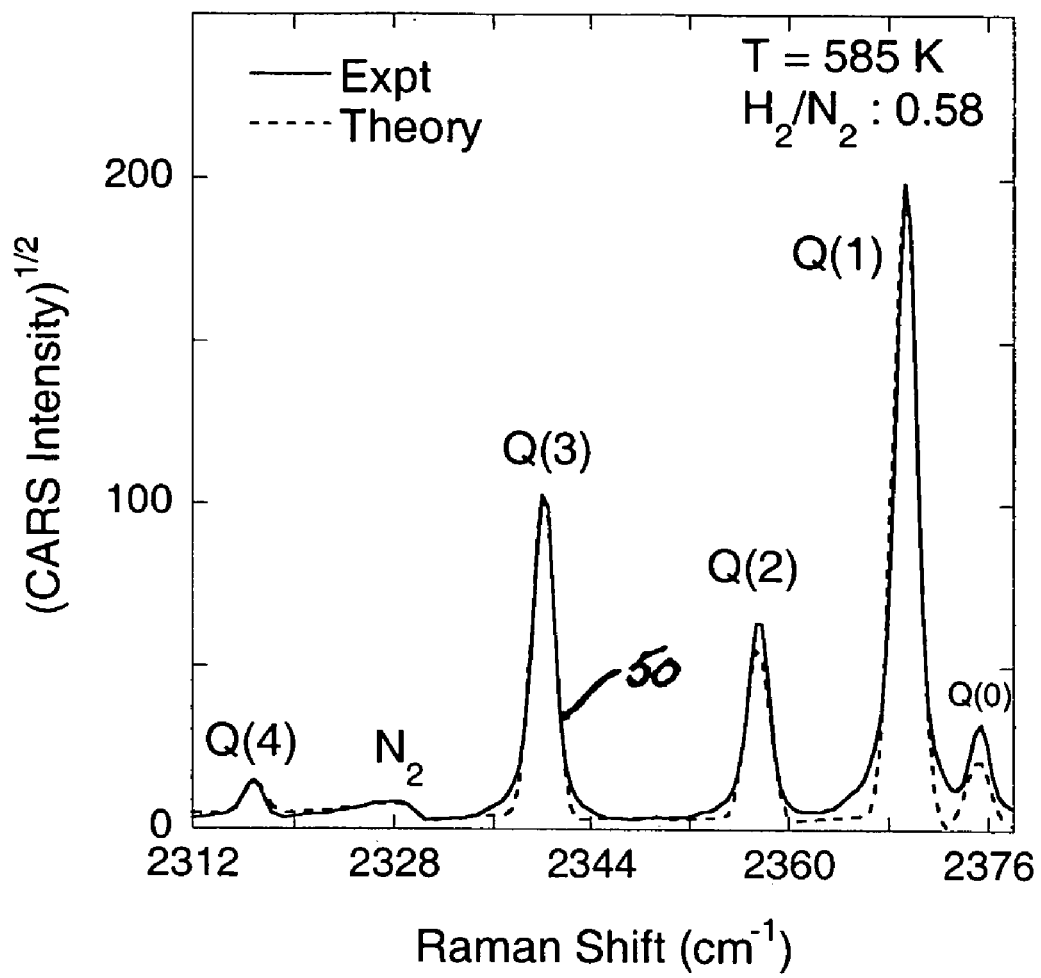
FIG. 5 is a $H_2$—$N_2$ CARS spectrum in an atmospheric-pressure hydrogen-air diffusion flame.

FIG. 5 shows an example of an $H_2$—$N_2$ CARS spectrum 50 (average of 10 laser shots) acquired on the lean side of an atmospheric-pressure hydrogen-air diffusion flame about 2 mm from the center of the nozzle and 0.5 mm above the nozzle lip. The CARS signal was generated with the 532-nm, 486-nm, and 607-nm incident beam combination. This signal appears near 437 nm, and the Raman shift is calculated based on the 486-nm laser beam. The Q-branch lines of the $H_2$ molecule and the rotational lines of the $N_2$ molecule are clearly evident in the spectrum shown in FIG. 5.

The invention therefore provides a novel triple-pump coherent anti-Stokes Raman scattering system for simultaneous measurements of temperature and species concentrations with high spatial and temporal resolution. It is understood that modifications to the invention may be made as might occur to one with skill in the field of the invention within the scope of the appended claims. All embodiments contemplated hereunder that achieve the objects of the invention have therefore not been shown in complete detail. Other embodiments may be developed without departing from the spirit of the invention or from the scope of the appended claims.

We claim:

1. A triple-pump coherent anti-Stokes Raman scattering system for simultaneous measurements of temperature and species concentrations with high spatial and temporal resolution in a gaseous system, comprising:
   (a) first and second pump lasers and first and second narrowband dye lasers for generating output beams near two substantially distinct wavelengths;
   (b) a broadband dye laser;
   (c) optical means for directing the output beam from said first pump laser onto said first narrowband dye laser and onto said broadband dye laser and for directing the output beam from said second pump laser onto said second narrowband dye laser;
   (d) optical means defining a probe region for receiving a gaseous sample and for directing the output beams from said first pump laser, said first and second narrowband dye lasers and said broadband dye laser through said probe region; and
   (e) detector means for detecting the optical output from said probe region.

2. The system of claim 1 wherein said first and second pump lasers are injection-seeded Nd:YAG lasers providing output beams respectively at about 532 nm and about 355 nm.

3. The system of claim 2 wherein said first and second narrow band dye lasers provide output beams respectively at about 554 nm and about 486 nm.

4. The system of claim 1 wherein the broadband dye laser generates an output beam at a frequency spectrum centered near 607 nm.

5. The system of claim 1 wherein said detector means includes a spectrometer and a charge coupled device.

* * * * *